United States Patent
Benz

(10) Patent No.: US 10,245,418 B2
(45) Date of Patent: Apr. 2, 2019

(54) APPARATUS FOR A MEDICAL SYSTEM INFLATION SYRINGE

(71) Applicant: Philip Benz, Portland, OR (US)

(72) Inventor: Philip Benz, Portland, OR (US)

(73) Assignee: Semler Technologies, Inc., Milwaukie, OR (US)

( * ) Notice: Subject to any disclaimer, the term of this patent is extended or adjusted under 35 U.S.C. 154(b) by 786 days.

(21) Appl. No.: 14/836,031

(22) Filed: Aug. 26, 2015

(65) Prior Publication Data

US 2016/0101269 A1  Apr. 14, 2016

Related U.S. Application Data

(60) Provisional application No. 62/061,513, filed on Oct. 8, 2014.

(51) Int. Cl.
| | |
|---|---|
| *A61B 17/135* | (2006.01) |
| *A61M 25/10* | (2013.01) |
| *A61B 5/022* | (2006.01) |
| *A61M 39/10* | (2006.01) |
| *A61B 17/00* | (2006.01) |

(52) U.S. Cl.
CPC ....... *A61M 25/10182* (2013.11); *A61B 5/022* (2013.01); *A61B 17/135* (2013.01); *A61B 2017/00544* (2013.01); *A61M 39/10* (2013.01)

(58) Field of Classification Search
CPC ................. A61M 25/10182; A61M 39/10
See application file for complete search history.

(56) References Cited

U.S. PATENT DOCUMENTS

| | | |
|---|---|---|
| 4,452,473 A | 6/1984 | Ruschke |
| 5,360,413 A | 11/1994 | Leason |
| 5,611,576 A | 3/1997 | Guala |
| 5,620,427 A | 4/1997 | Werschmidt |
| 5,651,776 A | 7/1997 | Appling |
| 6,089,541 A | 7/2000 | Weinheimer |
| 6,599,269 B1 * | 7/2003 | Lewandowski ..... A61M 5/3134 604/110 |
| 8,479,370 B2 | 7/2013 | Grant |
| 8,808,254 B2 | 8/2014 | Lynn |
| 2012/0150129 A1 * | 6/2012 | Jin .................. A61M 39/10 604/240 |
| 2013/0345587 A1 * | 12/2013 | Colman ........... A61M 39/1011 600/532 |

* cited by examiner

*Primary Examiner* — Diane D Yabut

(57) ABSTRACT

The medical system inflation syringe of the present invention enables a fluid communication selective interconnection of a male connector with a subset of certain female connectors, more particularly female Luer connectors, while preventing interconnection of said male connector with other subsets of female connectors, for the purpose of providing secure interconnection to achieve fluid (including gas or air) communication only with medical systems with which the inflation syringe is intended to be interconnected.

8 Claims, 11 Drawing Sheets

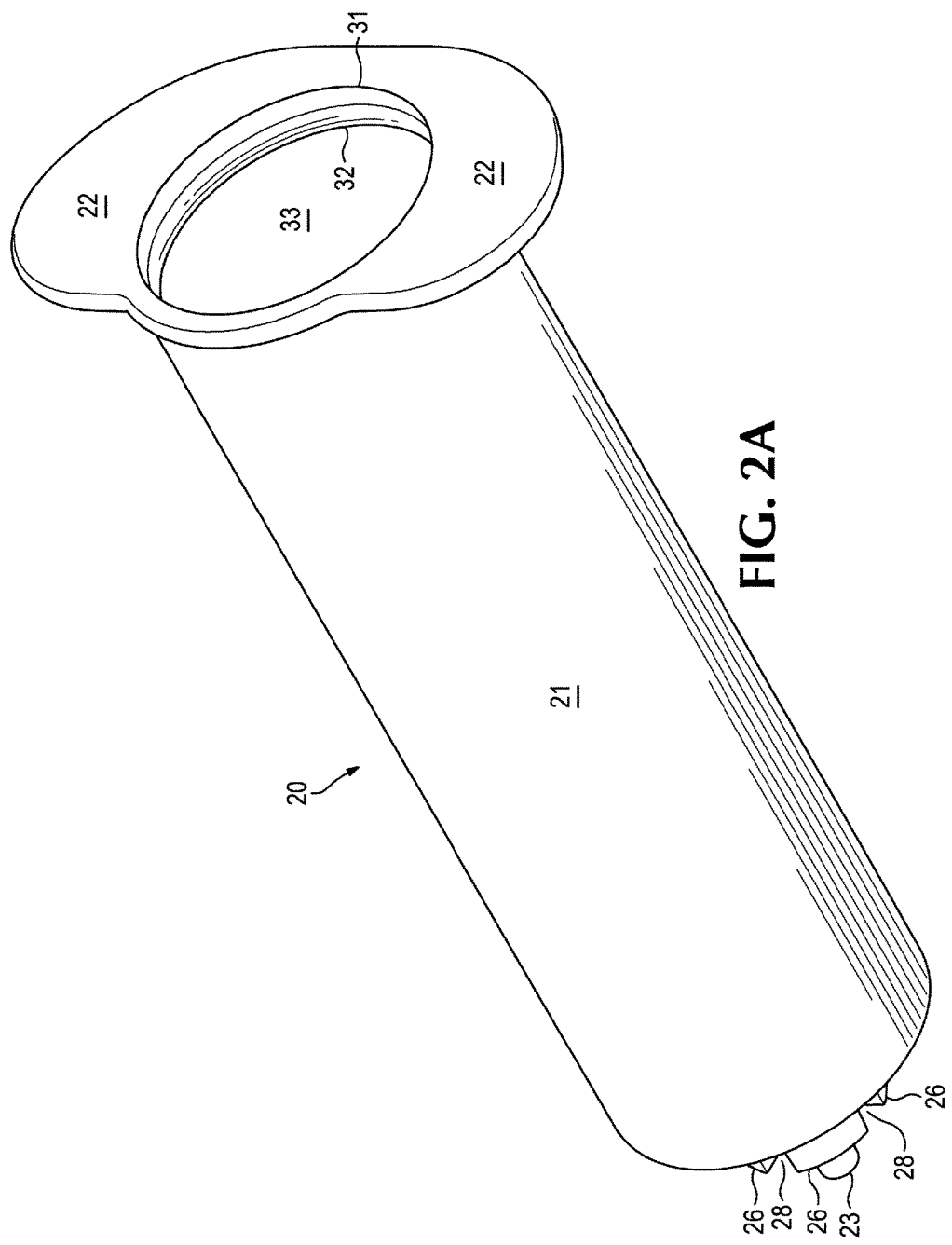

APPARATUS FOR A MEDICAL SYSTEM INFLATION SYRINGE

RELATED APPLICATIONS

This application claims priority to U.S. Provisional Patent Application Ser. No. 62/061,513 filed Oct. 8, 2014, the contents of which are incorporated herein in their entirety by this reference.

FIELD OF THE INVENTION

The field of the invention generally relates to syringes used for inflation, including those used in conjunction with medical devices. In particular, the invention relates to an inflation syringe for use in inflating and deflating inflatable medical devices in proximity or attached to a patient. More particularly the invention relates to an inflation syringe for use with an adjustable, inflatable wristband device for reducing or stopping blood flow in said blood vessels by means of adjustably applying compression to the body surface overlying said blood vessels, for the purpose of achieving post-procedure hemostasis at a vascular puncture site used to gain access for catheters or other cannulae to the circulatory system.

BACKGROUND OF THE INVENTION

The present invention is a syringe used for inflation of a separate device, more particularly a syringe removably attachable to a separate medical system. Syringes of varying sizes and purposes, and having varied means of connection to other medical devices and systems, are commonly used in the provision of medical care. Well known to clinicians, these syringes are used for liquids administration into liquid management systems such as intravenous fluid systems, injection into the body when coupled with a needle, and inflation of components of medical devices, for example balloons of catheters. Syringes, including that of the present invention, generally include a hollow barrel, a plunger that can be moved within the barrel to move fluid (including air or gas) in and out of the barrel, a plunger tip to seal the fluid or gas within the barrel, and a connector for coupling the syringe to and enabling fluid (including air or gas) communication with a separate device or system.

Examples of such connectors include Luer Slip or Luer Lock, which are often utilized in fluid flow conduits to achieve fluid-tight connection between the syringe and the device or system to which it is connected. These Luer connections are comprised of a male and a female member, the male member having a slightly tapered body and the female member having a similarly tapered bore for receiving the male member, such as those described in ISO 594 standards, more particularly ISO 594-1:1989 and ISO 594-2:1998(E), incorporated herein by reference. The male and female members may be locked together, for example, by threaded coupling as in the Luer Lock connections, or the connection between the two members may be only by a friction fit as in the Luer Slip connections. Luer Lock members have a thread, more particularly an internally threaded collar to lock the male and female members together, thus operating to prevent fluid leakage between the male and female members. Another purpose of the locking member is to maintain the interconnection between the male and female members when opposing pulling forces exerted on the equipment or tubing attached to these connectors attempt to pull them apart.

Exemplary Luer fittings are disclosed by U.S. Pat. Nos. 4,452,473, 5,611,576, 5,620,427 or 5,651,776 and others, virtually all of which relate to various means of locking the members together to prevent accidental separation. Lynn, in U.S. Pat. No. 8,808,254, discloses a Luer Lock fitting with an integral valve that includes an interior self-sealing slitted receiving septum that permits entry of a male Luer-tipped cannula and seals itself when said cannula is withdrawn. This is also known as a swabable valve, well known to those skilled in the art. Grant, in U.S. Pat. No. 8,479,370, discloses an adapter, having Luer connection features, the purpose of which is to prevent inadvertent interconnections between medical systems attached to a patient, the achievement of which could injure said patient, by means of an intervening locking component placed in line between two Luer connectors.

Typical Luer fitting members are often incorporated into medical systems or tubing having different purposes. For instance, one system may be directed toward enteral feeding, while another system may be directed toward intravenous fluid medication delivery, while yet another system may permit cannulation of a patient's vascular system. Conventional Luer fitting members are usually sized and shaped in accordance with the ISO 594 industry standards, regardless of intended use. For instance, Luer male and female connector members associated with different types of medical systems may be configured to have similarly sized inner diameters, outer diameters, lengths, thread sets, and/or other dimensions including the 6% taper, that permit secure, yet inadvertent interconnection. As a result, a male Luer fitting member for enteral feeding may be inadvertently interconnected with a female Luer fitting member associated with vascular cannulation, or vice versa. Another secure yet inadvertent interconnection example is the interconnection of a syringe for the purpose of injecting air into a balloon or cuff, e.g. on a catheter or external vascular compression device, to a cannula inserted into a blood vessel. Injury or death may occur due to mistaken administration of, in the prior example, air into a patient's vascular system, causing embolism. The inadvertent interconnection of portions of different types of systems may lead to system cross-contamination and/or erroneous medical fluid or gas delivery, thereby potentially putting the subject patient in jeopardy. This has been described in several health care publications, including "Tubing misconnections—a persistent and potentially deadly occurrence", JCAHO Sentinel Alert 36 (Apr. 3, 2006), and "Preventing Misconnections of Lines and Cables", ECRI Health Devices, March 2006, Vol. 35, Number 3.

A need therefore exists for a mechanism that prevents secure interconnection of medical systems having dissimilar intended uses. This may be achieved by including dissimilar sizes of the interconnecting elements or physical features that obstruct partial or complete interconnection. However, it is in some cases desirable to enable a selective interconnection of a male connector with a subset of certain Luer female connectors while preventing interconnection of said male connector with other subsets of Luer female connectors.

The present invention enables a selective interconnection of a male connector with a subset of certain connectors, more particularly female Luer connectors having a valve while preventing interconnection of said male connector with other subsets of connectors, more particularly female Luer connectors lacking such valve. The medical system inflation syringe includes a male connection means that further includes at least a nozzle. A preferred embodiment of such a male connection means more particularly includes outside diameters of the nozzle smaller than any specified in the ISO 594 Luer standards along the entire length of the nozzle, thereby enabling selective interconnection only with certain female Luer connectors, more particularly those having swabable valves, which include a silicone or other elastomeric insert, the insertion of a nozzle into which opens it and the withdrawal of the nozzle closing it; such swabable valves are well known to those skilled in the art, for example, the Halkey-Roberts RobertSite® valve (U.S. Pat. Nos. 5,360,413 and 6,089,541). The male connection means of the present invention further prevents secure interconnection with other female Luer connectors, more particularly those that do not include a swabable valve. The male connection means thus enables fluid communication selective interconnectability to other medical systems or devices by achieving secure interconnection with certain female connectors and by its design preventing secure interconnection with others.

The medical system inflation syringe of the present invention is generally intended to be used to inflate and deflate a balloon or other inflatable compartment to which it is attached, i.e. enable fluid (including gas or air) communication with said balloon or inflatable compartment. This inflation syringe may be used for a variety of similar purposes, more particularly the inflation and deflation of at least one balloon on an external vascular compression device. Examples of such devices include the Terumo TR-Band, the VascBand distributed by Vascular Solutions, Inc., and the invention by Benz and Semler described in pending U.S. application Ser. No. 14/329,080. This inflation syringe further includes ergonomic features for easier use by an operator for inflation and deflation, more particularly injecting a pre-measured amount of air into a balloon, adjusting, i.e. increasing or decreasing, volume of air in a balloon, and completely removing air from a balloon.

Since many medical procedures are performed where infection of the subject patient is a significant risk and interconnection with sterile medical systems is expected, microbe-free operation is a desirable characteristic of the inflation syringe. The inflation syringe is capable of optionally being sterilized so as to provide a sterile, uncontaminated instrument to the operator can be disposed of after a single use to avoid cross-contamination from patient to patient.

An objective of the inflation syringe is to enable secure interconnection to achieve fluid (including gas or air) communication with certain other medical systems, i.e. those having a female connector that includes a swabable valve, while preventing secure interconnection with medical systems having a female connector that do not include a swabable valve, in particular those female connectors that comply to the ISO 594 Luer standards.

Another objective of the inflation syringe is making more convenient the operation of the syringe by an operator while injecting air into a balloon of an interconnected medical system, adjusting volume of air in a balloon, and completely removing air from a balloon.

Another objective of the inflation syringe is its low cost of acquisition and use by an operator, to enable cost-effective disposability, while providing for safe operation as a sterile device.

The inflation syringe of the present invention achieves these objectives as shown in the Detailed Description of the Preferred Embodiments.

BRIEF DESCRIPTION OF THE DRAWINGS

FIG. 2A is a rear perspective view of a barrel 20.
FIG. 7 is a perspective view of an alternative nozzle 23a.
FIG. 8 is a bottom view of an alternative nozzle 23a.
FIG. 9 is a side section view with parts removed for clarity of an alternative nozzle 23a.

DETAILED DESCRIPTION OF THE PREFERRED EMBODIMENTS

Figure 1:
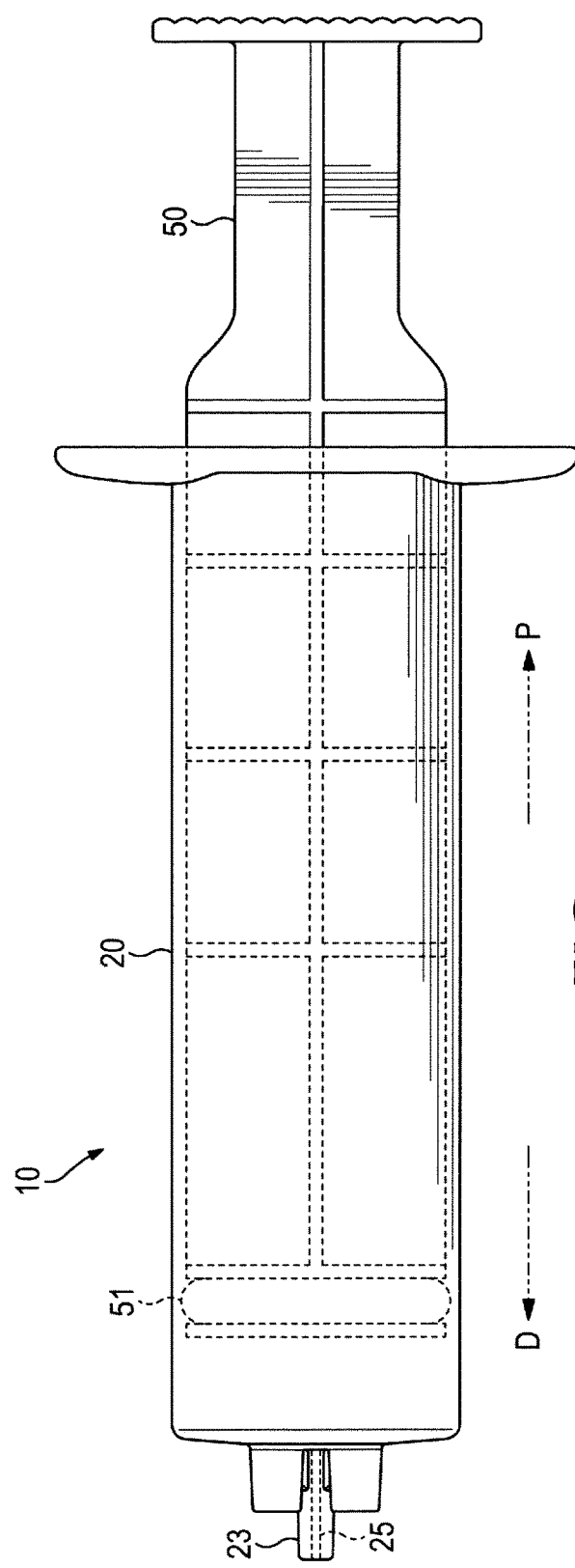
FIG. 1 is a side view of an inflation syringe 10 with parts removed for clarity.

A medical system inflation syringe 10 that enables secure selective interconnection to achieve fluid (including gas or air) communication with certain medical systems or devices, i.e. those having a female connector that includes a swabable valve, while preventing secure interconnection with medical systems having a female connector that do not include a swabable valve, is for use by an operator to inject air into at least one component of an interconnected medical system or device, adjust the volume of air in the at least one component, and completely removing air from the at least one component, the at least one component more particularly being an inflatable balloon. This inflation syringe 10 thus has the characteristic of fluid communication selective interconnection, and is shown in the drawings and Detailed Description included herein as preferred embodiments of the present invention. Although parts are described as discrete components and features are described with specific structures, it will be understood by those skilled in the art that alternative means of construction to achieve the same purpose may be employed without deviating from the present invention.

FIG. 1 shows a side view with parts removed of an embodiment of a syringe 10 that generally includes at least: a barrel 20, a plunger 50, the barrel 20 and plunger 50 each having distal D and proximal P ends. Also shown at the distal D end of the barrel 20 is a nozzle 23 having a lumen 25. An o-ring 51 serving the function of a plunger tip to enable a secure seal at the proximal end of the barrel 20 is shown attached to the plunger 50, which is shown fully inserted into the barrel 20. The plunger 50, by operation of an operator, slidably moves within the barrel 50 in the proximal P to distal D direction or vice versa. As the plunger 50 so moves, the interior volume of the barrel 20 changes, increasing when the plunger 50 moves proximally P and decreasing when it moves distally D, the o-ring 51, or alternatively a different type of plunger tip, seals the proximal P end of the barrel permitting passage of fluid (including air or gas) only through the lumen 25 of the nozzle 23.

FIG. 2A shows a rear perspective view of a barrel 20, which includes on its proximal end a proximal opening 31, an annulus 32 circumscribing the proximal opening 31, the barrel lumen 33, barrel tube 21, flanges 22, and components of the male connection means, including the nozzle 23, tabs 26, and vents 28.

Figure 2B:
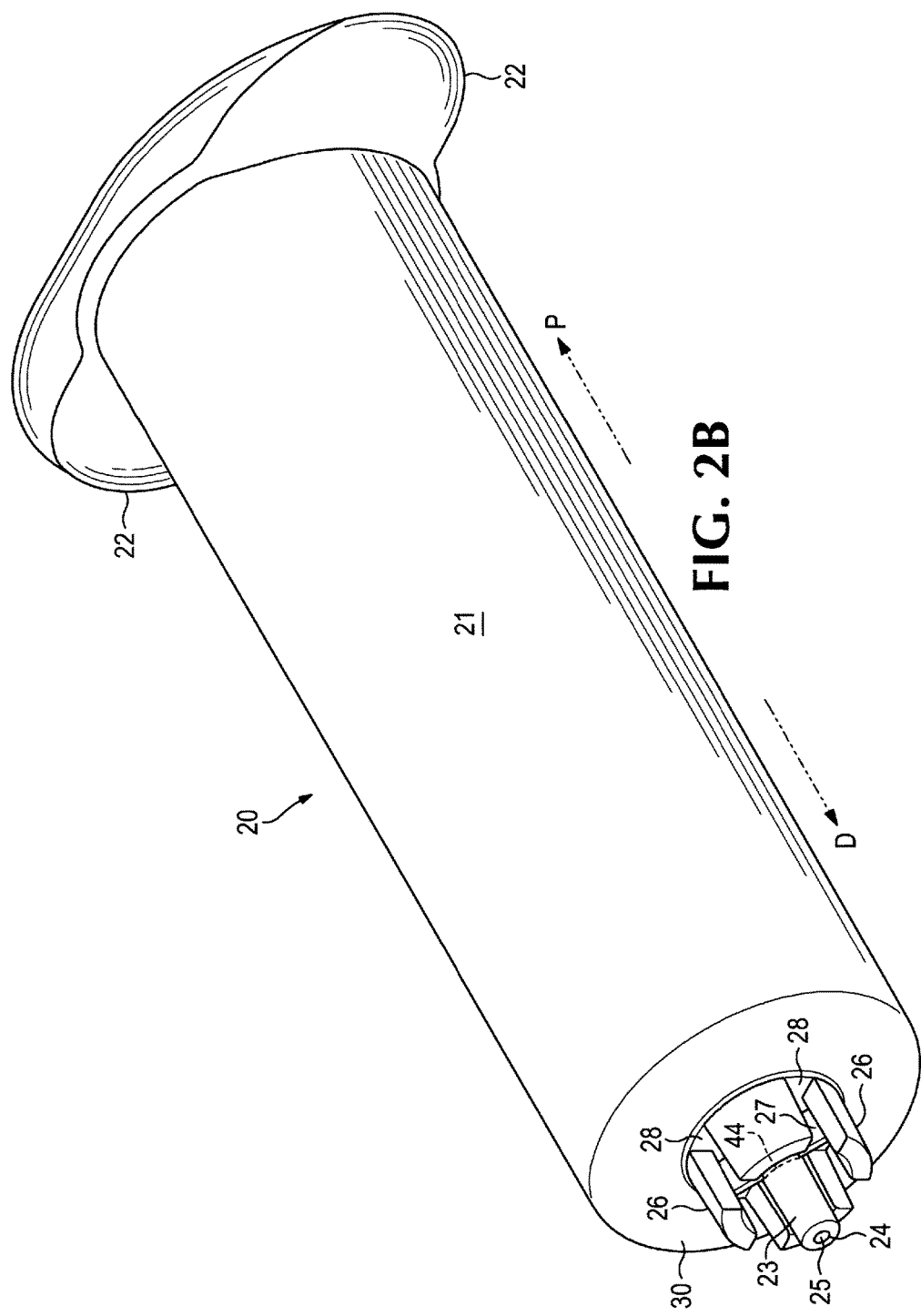
FIG. 2B is a top perspective view of a barrel 20.

FIG. 2B shows a top perspective view of the barrel 20, which has a proximal P end and distal D end and includes a barrel tube 21, barrel flanges 22 located at the proximal P end of the tube 21, and a male connection means located on the distal end 30 of the tube 21, the male connection means comprising at least a nozzle 23, a distal opening 24, a lumen 25, shroud tabs 26, standoff ribs 27, vents 28, and an insertion outside diameter 44 measured where the topmost (most distal) portion of the standoff rib 27 connects to the nozzle 23. The male connection means is shown to be formed as a unitary element of the barrel 20, for example, if the barrel 20 is composed of molded plastic the male communication means would be molded together with other elements of the barrel 20. Alternatively, the male communication means could be formed separately from a syringe or syringe barrel and attached thereto as an adapter or accessory part.

Figure 3:
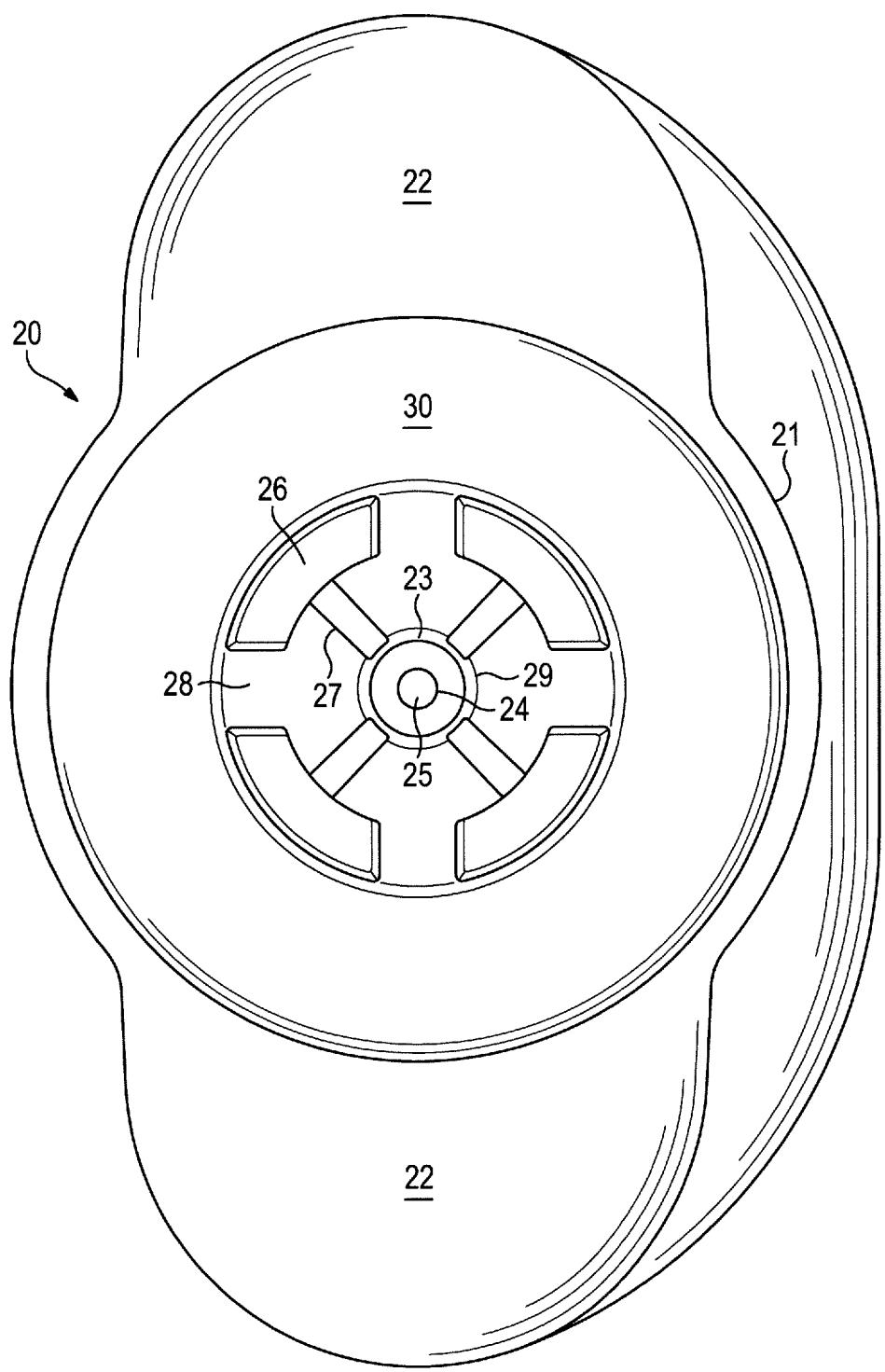
FIG. 3 is a distal end view of a barrel 20.

FIG. 3 shows an end view of the distal end 30 of the barrel 20, the tube 21 and the flanges 22. Located on the distal end 30 of the barrel 20 are components of the male connection means, including the nozzle 23, lumen 25 seen through the distal opening 24, at least one tab 26, at least one standoff rib 27 and at least one vent 28. The nozzle base 29 connects the nozzle 23 to the distal end 30.

Figure 4A:
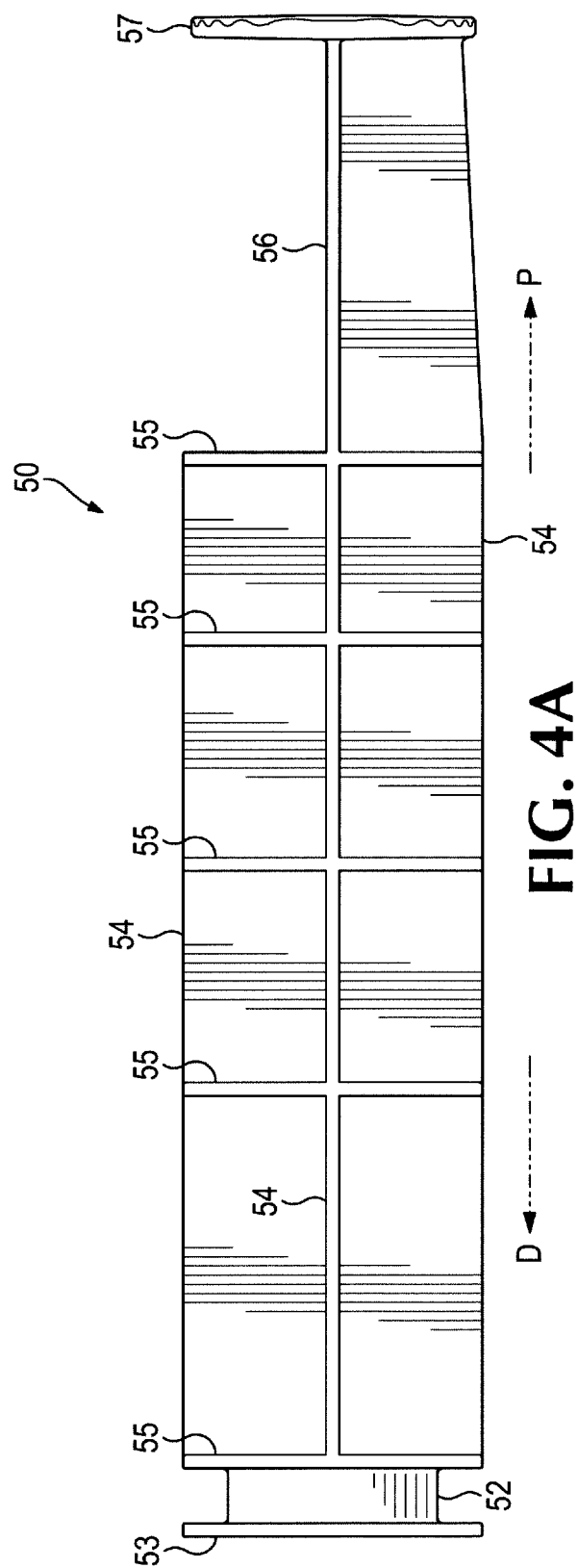
FIG. 4A is a side view of a plunger 50.

FIG. 4A shows a side view of a plunger 50 that has distal D and proximal P ends, an o-ring slot 52, distal plunger end 53, ribs 54, reinforcing discs 55, thumbrest 56 and plunger head 57.

Figure 4B:
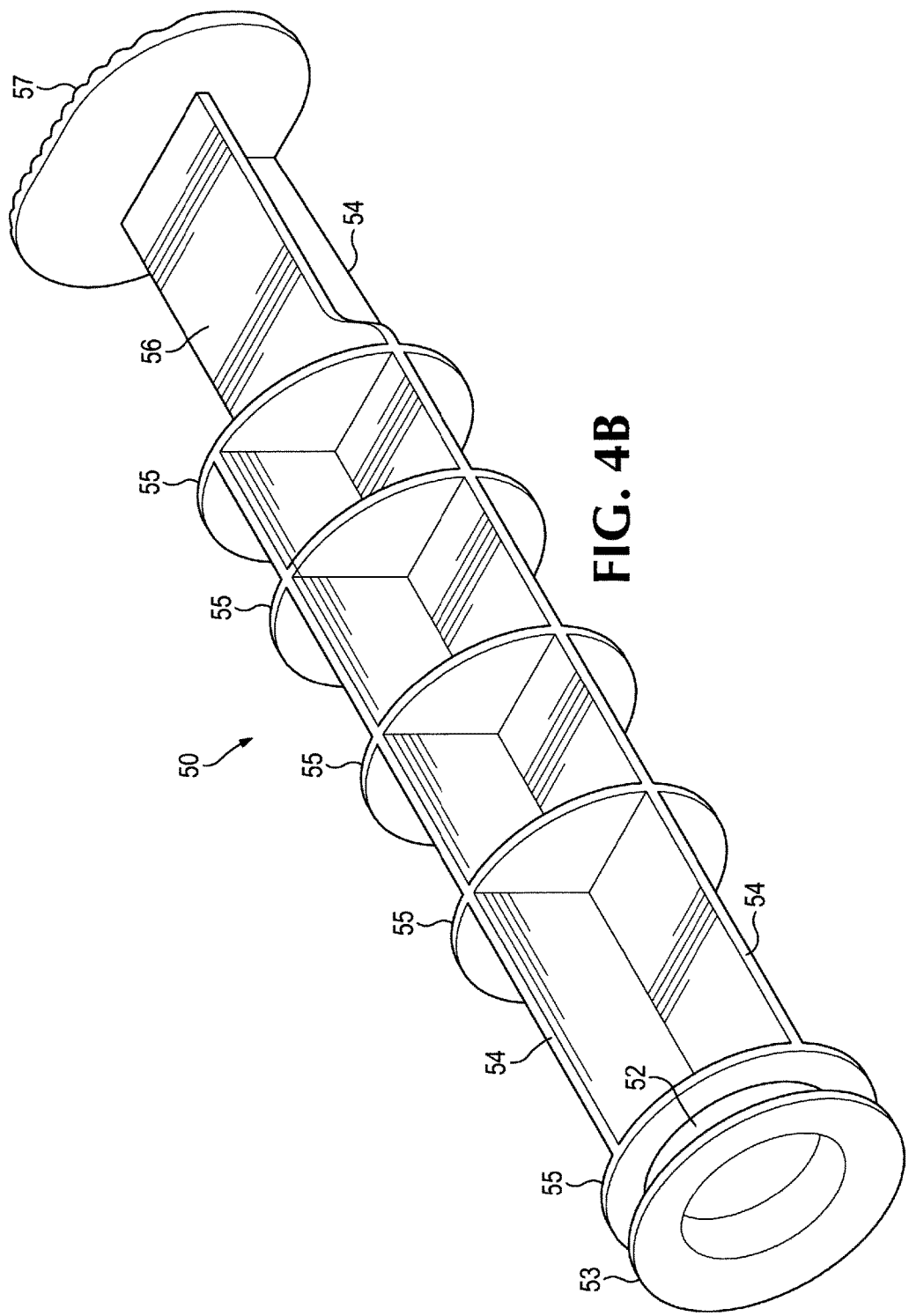
FIG. 4B is a top perspective view of a plunger 50.

FIG. 4B shows a top perspective view of a plunger 50 that includes an o-ring slot 52, a distal plunger end 53, at least one rib 54, at least one reinforcing disk 55, at least one thumbrest 56, and a plunger head 57. Not shown attached to the plunger 50 in this view is the o-ring 51.

Figure 5:
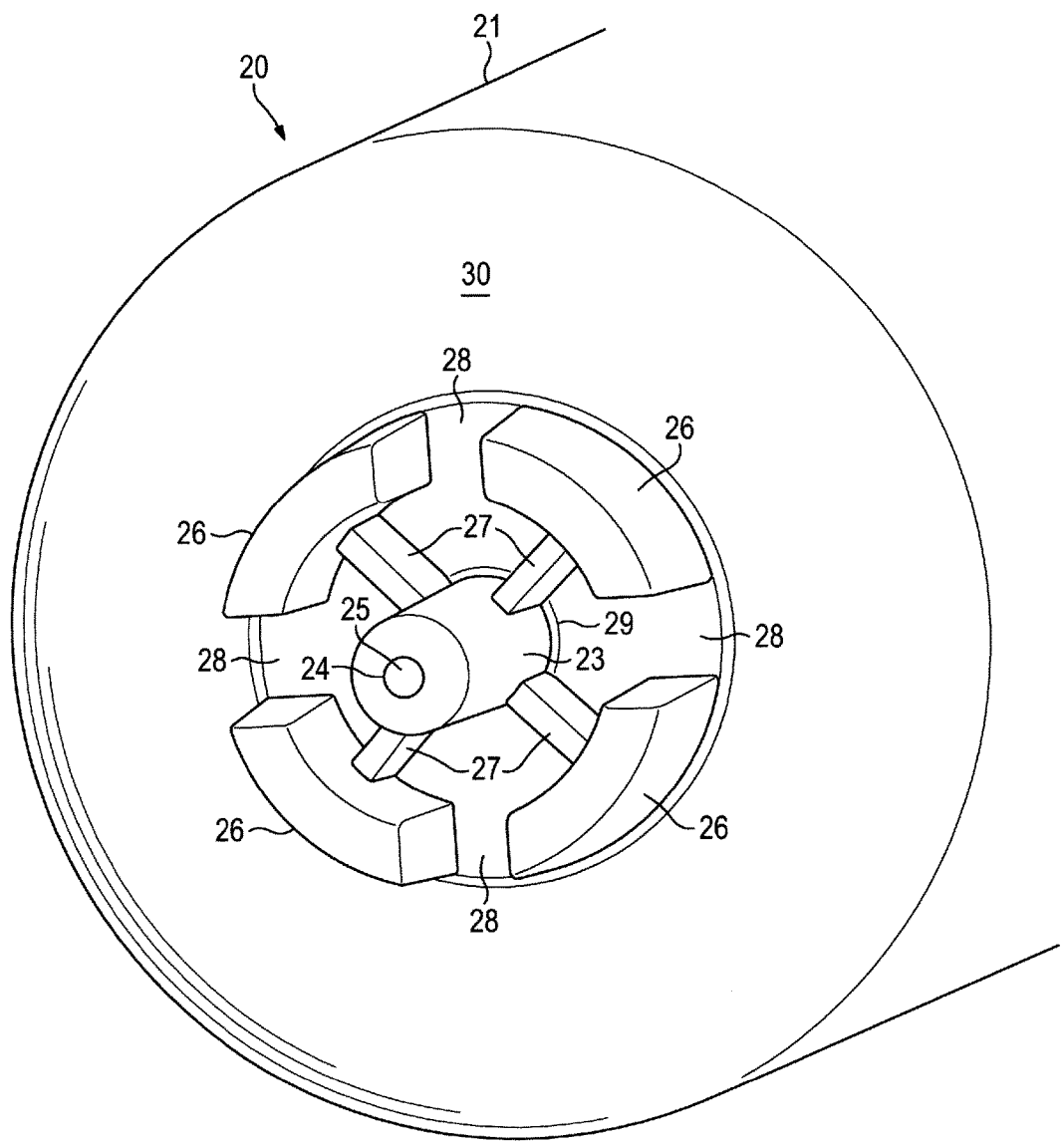
FIG. 5 is a front perspective view of the male connection means.

FIG. 5 shows a perspective end view of the male connection means located on the distal end 30 of the barrel 20, the male connection means including at least a nozzle 23 and at least one vent 28. The male connection means may further include a nozzle lumen 25 seen through the distal opening 24, shroud tabs 26, standoff ribs 27, and the nozzle base 29. The distal end 30 is located on the barrel tube 21. It can be seen that the height of the standoff ribs 27 is less than that of the shroud tabs 26. Although there are four each shown of the shroud tabs 26, standoff ribs 27, and vents 28, there is no requirement for a particular number provided at least one of each is present.

Figure 6:
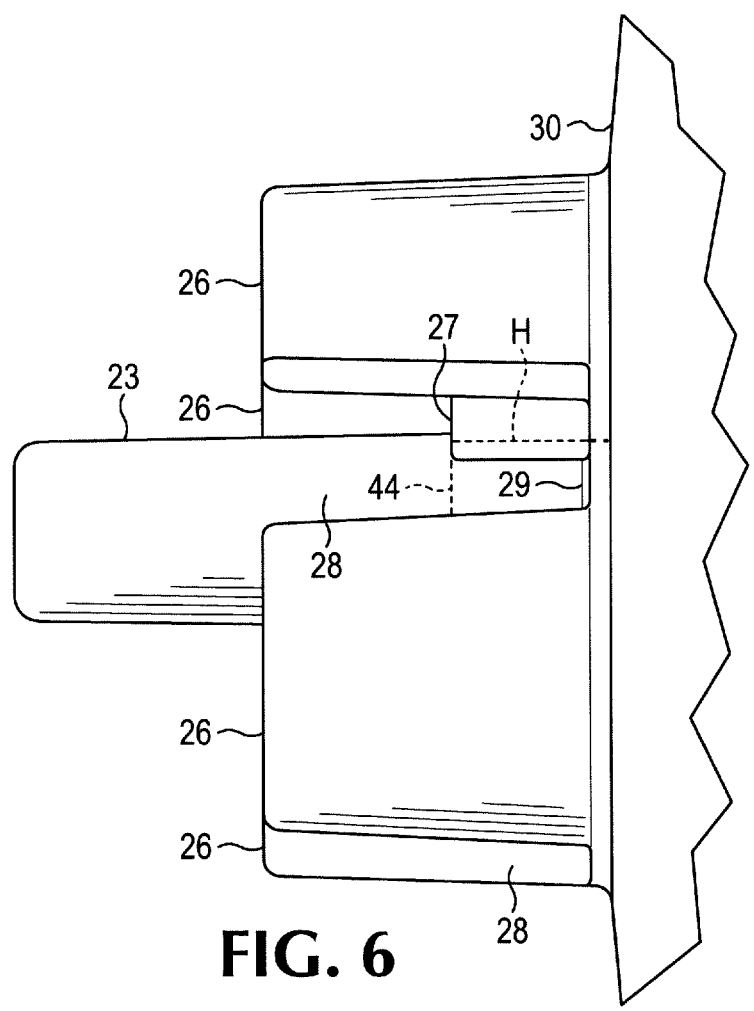
FIG. 6 is a side view of the male connection means.

FIG. 6 shows a side view of the male connection means, with the following components shown: nozzle 23, shroud tabs 26, standoff rib 27 having a maximum height H extending from the surface of the distal end 30 to the most distal surface of each standoff rib 27, a vent 28, and nozzle base 29. At the top or distal end of maximum height H, on the nozzle 23, is the insertion outside diameter 44.

Figure 7:
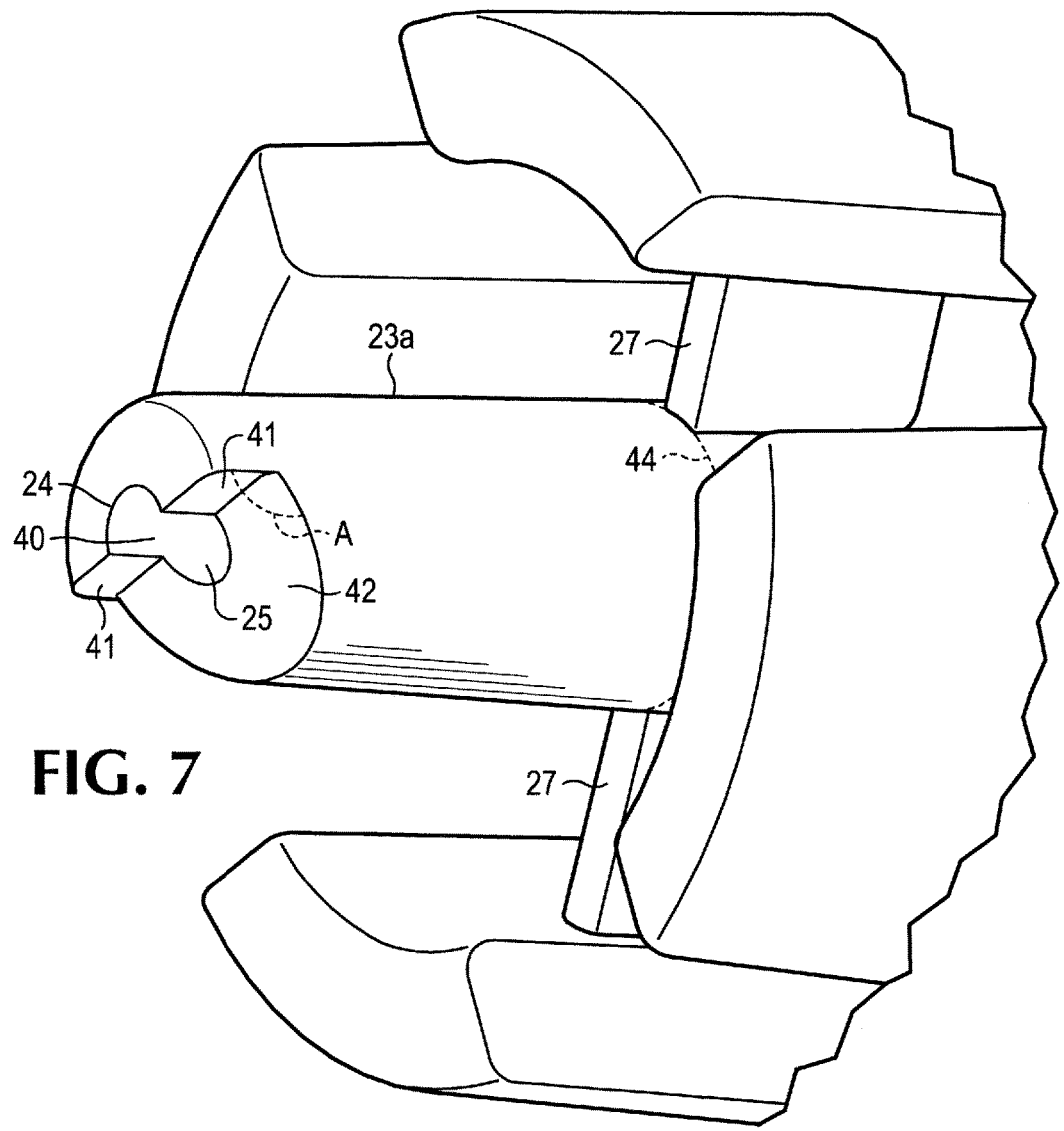

FIG. 7 shows a perspective view of an alternative nozzle 23a of a male connection means, with its following components shown: distal opening 24, lumen 25, a lumen sidecut 40 at the tip of the nozzle 23a, sidecut surrounds 41, and a sidecut face 42, cut at an angle A from the longitudinal axis of the nozzle 23a, and an insertion outside diameter 44 measured where the topmost (most distal) portion of the standoff rib 27 connects to outside wall of the nozzle 23a. Angle A is in the general range of 90° to 179°, more particularly in the range of 110° to 160°.

Figure 8:
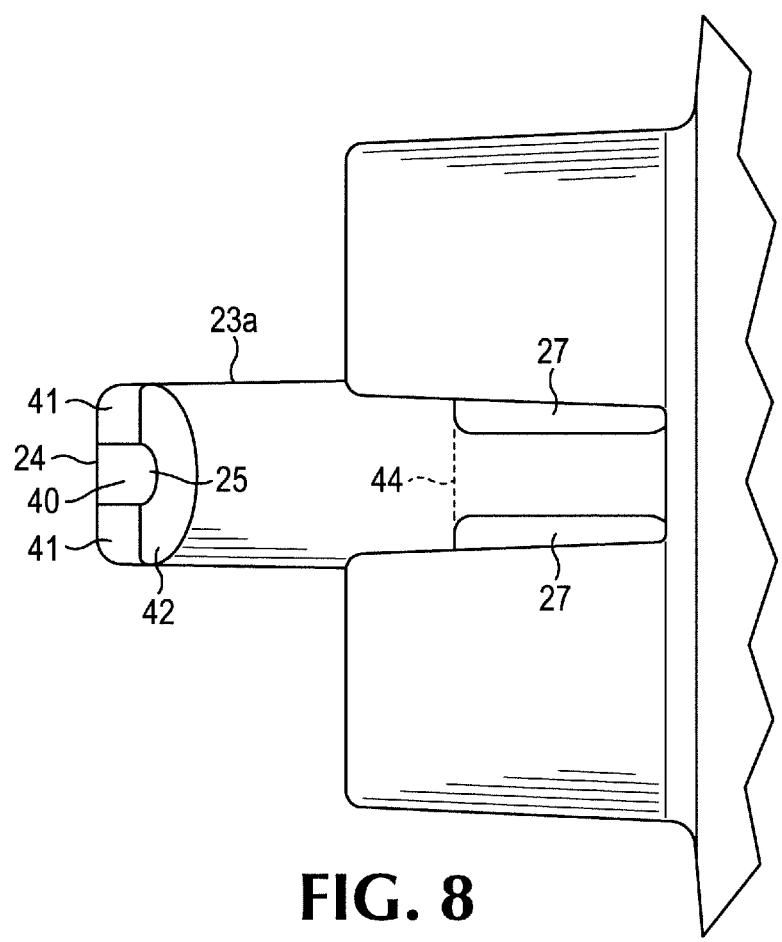

FIG. 8 shows a bottom view of an alternative nozzle 23a, including a distal opening 24, lumen 25, lumen sidecut 40, sidecut surrounds 41, a sidecut face 42 and an insertion outside diameter 44 measured where the topmost (most distal) portion of the standoff ribs 27 connects to the nozzle 23a.

Figure 9:
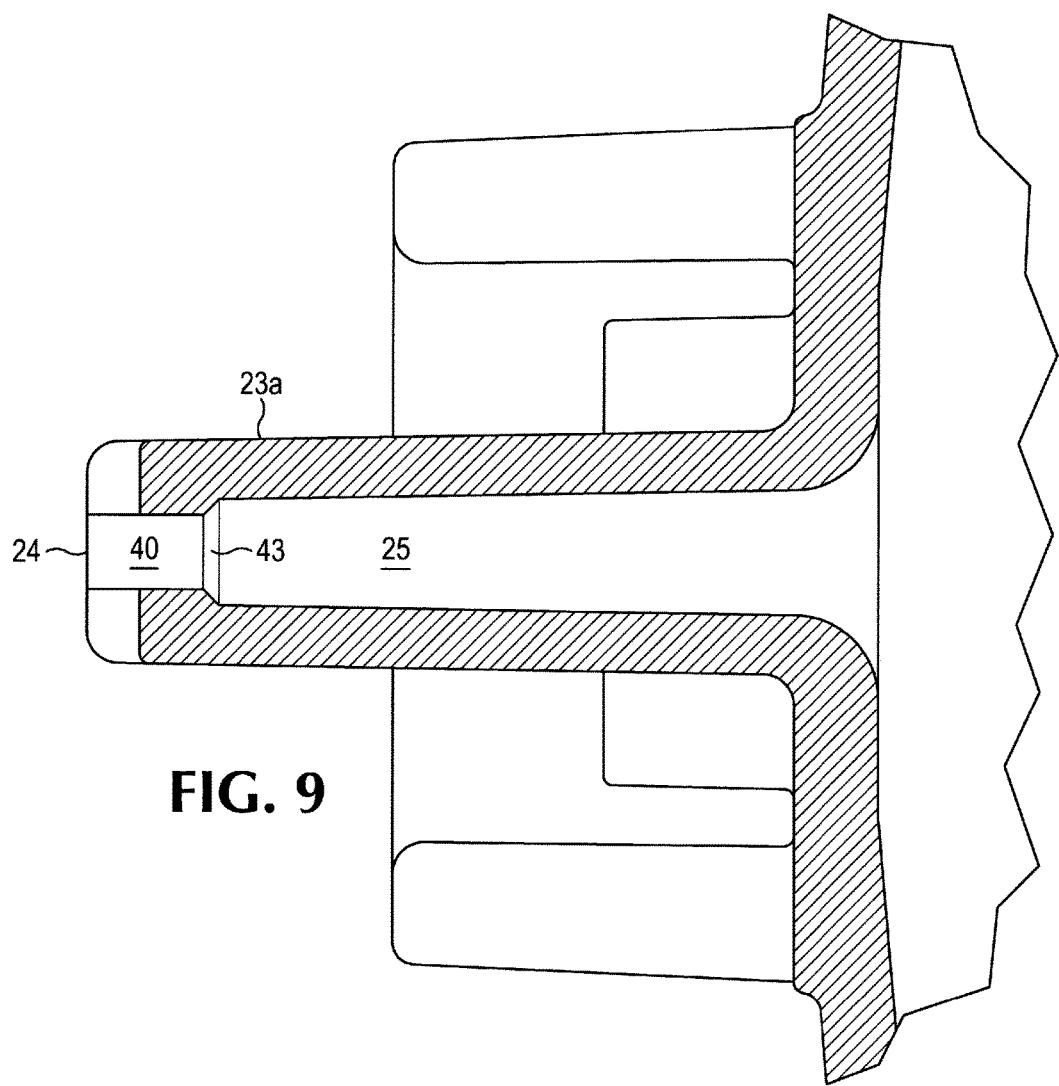

FIG. 9 shows a bottom section view, with parts removed for clarity, of an alternative nozzle 23a that includes a distal opening 24 in fluid connection with lumen 25 through the lumen sidecut 40 and lumen shoulder 43. Although the lumen shoulder 43 is shown as part of alternative nozzle 23a, it may also be present in nozzle 23.

When the syringe 10 is assembled, the plunger 50, with a plunger tip placed at the distal plunger end 53, more particularly o-ring 51 fitted into the o-ring slot 52, is inserted through the proximal opening 31 into the barrel lumen 33, through which the plunger 50 may slidably move. The annulus 32, having a slightly smaller inside diameter than the barrel lumen 33, permits passage of the o-ring 51 mounted on the plunger 50 because of the o-ring's 51 compressibility, and provides a stop to prevent inadvertent withdrawal of the plunger 50 from the barrel 20 when drawing air into the barrel lumen 33 by moving it in the proximal P direction.

Features on the plunger 50 that distinguish the present invention from the prior art include the thumbrest 56. This is useful to the operator since the actions related to inflation and deflation require both moving the plunger 50 in the distal D direction for inflation and moving it the proximal P direction for deflation, both actions required for the operation of a medical device, for example an inflatable compression device. The thumbrest 56 enables an operator to more move plunger 50 in the proximal P direction.

The syringe plunger 50 may be formed from a variety of materials, primarily thermoplastics used in injection molding that in finished form are generally rigid. These include nylon, polycarbonate, PVC, polypropylene, or ABS. The ribs 54 and reinforcing disks 55 provide rigidity to the plunger 50 by reducing axial deformation in response to twisting forces applied at the ends of the plunger 50. In the embodiment shown, the disks 55 have a round perimeter only slightly smaller than the lumen of the barrel lumen 33, as does the diameter of the ribs 54, so as to reduce lateral motion of the proximal P end of the plunger 50 during its slidable movement. However, it is within the scope of the invention that there may be different numbers, dimensions or shapes of the ribs 54 and disks 55 located on the plunger 50.

The o-ring 51 has the characteristic of compressibility, being formed of material having this characteristic, for example a silicone, fluorosilicone, nitrile, rubber, or other elastomer, these materials having a Shore A hardness of between 30 durometer and 90 durometer, more particularly between 40 durometer and 80 durometer. Further the o-ring 51 may include a lubricant, which can include an impregnation of wax or a coating of silicone or PTFE or other lubricating material, for the purpose of enhancing lubricity when slidably moving in the barrel lumen 33. It is understood by those skilled in the art and within the scope of this invention that any plunger tip having a shape other than an o-ring 51 and having the purpose of sealing the barrel lumen 33 may be incorporated into an embodiment of the syringe 10, and such plunger tips are in use in other commercially available syringes (for example, by Becton-Dickinson, Merit Medical, Exel, and others) as of the writing of this application.

The syringe barrel 20 may be formed from a variety of materials, primarily thermoplastics used in injection molding that in finished form are generally rigid. These include nylon, polycarbonate, PVC, polypropylene, or ABS. It is preferable that at least the barrel 20 be formed of a material having the characteristic of transparency or translucency.

Features on the barrel 20 that distinguish the present invention from the prior art include the outside diameters of the nozzles 23 and 23a, the lumen sidecut 40 of the nozzle 23a, the shroud tabs 26, standoff ribs 27, and vents 28.

The nozzles 23 and 23a have a taper similar to those found on nozzles complying with the ISO 594 standard, which is 6%. However these nozzles 23 and 23a have outside diameters smaller than specified in the ISO 594 standards along their entire lengths, i.e. from less than 3.990 millimeters at its narrowest to less than 4.270 millimeters at its widest, as disclosed in the standard (intermediate outside diameters between narrowest and widest along a nozzle length are calculated by applying a 6% taper). The outside diameters of the nozzles 23 and 23*a* deviate from the ISO 594 standard, in particular at insertion outside diameter 44, so as to prevent an airtight sealing fit between the nozzles 23 or 23*a* and a female Luer connector that lacks a swabable valve, thereby permitting air injected by syringe 10 to backflow around the nozzles 23 or 23*a* while inserted into the female Luer connector, while achieving an airtight sealing fit with a female Luer connector having a swabable valve.

The nozzle 23*a* further includes a lumen sidecut 40, that permits air being injected from the syringe 10 to escape not only from the distal opening 24, as is generally the design of male Luer connectors, but from the lumen sidecut 40 as well. This helps prevent air injection into a medical system through a female Luer connector that lacks a swabable valve and that may have a narrowing inside diameter that may create an airtight sealing fit with a male Luer connector nozzle; in this event air passing through nozzle 23*a* would escape through the lumen sidecut 40 and backflow around the nozzle 23*a* and out of the female Luer connector.

Standoff ribs 27 limit the extent to which the nozzle 23 or 23*a* may be inserted into a female Luer connector, while permitting sufficient insertion into a swabable valve, for example, the Halkey-Roberts Robertsite series 245 valve to achieve an airtight sealing fit, such that the outside diameter of the nozzle 23 or 23*a* at the entry of the female Luer connector is the insertion outside diameter 44. Thusly limiting the extent of nozzle insertion into a female Luer connector further helps avoid the risk of having a sealing fit i) between a narrowing of the inside diameter of the female Luer connector and the tip of the nozzle 23 or 23*a*, and ii) between the rim of a female Luer connector and the distal end 30 of the barrel 20 or nozzle base 29.

The shroud tabs 26 help enable a friction fit between the interior surface of the tabs 26 and exterior diameter of female Luer connector, more particularly a connector having a swabable valve, for example, the Halkey-Roberts series 245 valve. This helps the operator keep the syringe 10 in place on the swabable valve during operation by reducing opportunity for accidental disconnection. This embodiment includes a non-locking male connection means, i.e. it excludes a locking mechanism such as a Luer Lock.

The vents 28 enable the backflow of air that escapes from the female Luer connector, i.e. not a swabable valve, when air is injected from the syringe 10 to flow out of the male connection means. An alternative embodiment of the syringe 10 may have shroud tabs 26 connected at their distal ends to each other and in this embodiment the vents 28 would not have an open end, but instead would appear as holes open to opposite sides of the shroud tabs 26. Alternatively, a vent 28 may comprise a hole extending from the interior of the sidewall of the nozzle 23 or 23*a* through to its exterior sidewall, said hole being located at or distal to the nozzle base 29, and having a diameter smaller than the distal opening 24, so as to enable backflow of air out of the nozzle 23 or 23*a* when meeting resistance inside the connected medical device or system. A vent 28 comprising such hole in the nozzle 23 or 23*a* sidewall may be present in the absence of standoff ribs 27.

When fitted into a female Luer connector that is not a swabable valve, the maximum outside diameter of the nozzle 23 or 23*a* at the top of the standoff rib 27 that prevents further insertion into the connector is insertion outside diameter 44. The minimum inside diameter of said female Luer connector according to the ISO 594 standard is 0.1681 inches or 4.270 millimeters. The insertion outside diameter 44 is smaller than the 0.1681 inches by an extent so as to permit generally free backflow of air from the distal opening 24, on meeting resistance within said connector or anywhere downstream, e.g. in the attached medical system, around the nozzle 23 or 23*a* and out of the connector. The range of dimensions of the insertion outside diameter 44 is less than 0.1681 inches, generally in a range of 0.0250 inches to 0.1680 inches, more particularly in a range of 0.0750 inches to 0.1500 inches. Preferred embodiments may have an insertion outside diameter 44 in the range of 0.0900 inches to 0.1200 inches. An insertion outside diameter 44 having a dimension of 0.1200, for example, provides approximately half of the area of the female Luer connector opening through which air can backflow.

The lumen 25 of the nozzle 23 or 23*a* may have an inside diameter that varies along its length. For example, it may taper along its length, narrowing at the distal opening 24, and varying in a range of 0.0100 inches to 0.1000 inches. A lumen shoulder 43 may neck down the lumen 25 instead of or in addition to the lumen 25 having a tapered shape, that may generally correspond to the outside diameter of the nozzle 23 or 23*a* at each point along its length so that the nozzle 23 or 23*a* walls are of generally consistent thickness. A smaller distal opening 24 necessarily limits the passage of air under injection therethrough compared to a larger distal opening 24. The range of dimensions of distal opening 24 is generally in the range of 0.0100 inches to 0.1000 inches, more particularly in the range of 0.0200 inches to 0.0600 inches. Preferred embodiments may have a distal opening 24 dimension of less than 0.0500 inches, more particularly between 0.0300 inches and 0.0400 inches.

The vents 28 permit air backflowing out of the loose connection between the nozzle 23 or 23*a* and a female Luer connector not having a swabable valve to exit entirely from the male connection means. The vents 28 have no necessary number or dimension, except that the combined vent 28 area be not less than the area of the distal opening 24. The area of a vent 28 is the space bounded by the distal end 30, the edges of the immediately adjacent shroud tabs 26 and the rim of the female Luer connector.

The nozzle lumen 25, located inside the nozzle 23, connects the barrel lumen 33 of the barrel 20 to distal opening 24. When the plunger 50 is moved under force in the proximal P direction, air is withdrawn into the tube 21 through the lumen 25, through the distal opening 24. Conversely, when the plunger 50 is moved in the distal D direction, the air within the tube 21 is forced through the lumen 25, through the distal opening 24 out of the syringe 10. In the event that the male connection means is inserted into a female Luer connector having a swabable valve, a secure seal, i.e. permitting no leakage, is established and all of the air is injected from the syringe 10 through this interconnection into the medical system attached to this female Luer connector. The tabs 26 provide a securement function to the male connection means by enabling a friction fit with the outside diameter of a female Luer connector.

Thus, in the event that the male connection means is inserted into a female Luer connector lacking a swabable valve and the tabs 26 achieve a friction fit with the exterior of the female Luer connector, a secure seal is not established because the outside diameter of nozzle 23 or 23*a*, at insertion outside diameter 44, is smaller than the inside diameter of the female Luer connector. Thus, depending on the resistance inside the medical system to inflowing air, all or a significant portion of the air injected from the syringe 10 through this interconnection will backflow, i.e. exit the medical system through the female Luer connector and around the exterior surface of the nozzle 23 or 23*a*. The vents 28 enable air backflowing out of an attached female Luer connector around the exterior surfaces of the nozzle 23 to vent outside the syringe 10 and the medical system. The distal surface of the standoff ribs 27 is raised above the distal end 30 of the barrel by a height H, so that the rim of a female Luer connector comes into contact with this standoff rib 27 instead of the distal end 30, thus precluding a secure seal either with the distal end 30, the base 29 or the largest outside diameter of the nozzle 23 or 23*a*, i.e. at insertion outside diameter 44. Therefore, in the event that the male connection means is inserted into a female Luer connector lacking a swabable valve, a secure seal is not established and the air backflows from the medical system through this female Luer connector, past the nozzle 23 or 23*a* and through the vents 28, helping to preclude inadvertent intrusion into a medical system or body part not intended to have air injected into it.

The exterior dimension of the nozzle 23 or 23*a*, the interior diameter of the distal opening 24, and the height of the standoff ribs 27 enable the selective interconnectability of the syringe 10 to other medical systems or devices, i.e. achieving fluid (including gas or air) communication with those having a female connector that includes a swabable valve, while preventing secure interconnection with medical systems having a female connector that do not include a swabable valve. The exterior dimension of the nozzle 23 or 23*a* enables its secure interconnection into a female Luer connector having a swabable valve, however such dimensions, in particular its outside diameter, are too small to achieve secure interconnection with standard Luer connectors that have no valve inserts. Further, the interior diameter of the distal opening 24 is smaller than common Luer syringes, thus limiting the volume of air that can be transferred when it is expelled from the tube 21 under a given force exerted upon the plunger 50 to move it in the distal direction D. Notably, the male connection means of the present invention does not comply to the ISO 594 standard, in particular with respect to the outside diameters of the 6% male conical fitting and more particularly at insertion outside diameter 44. In addition, the height of the standoff ribs 27 prevents a rim of a female Luer connector from coming into contact with the distal end 30 of the barrel 20, thus preventing a secure seal between the male connection means and the female Luer connector. When thusly inadvertently connected, on meeting resistance inside the connector, inside the medical system or elsewhere downstream, the air injected by the syringe 10 backflows out of the female Luer connector past the outside surface of the nozzle 23 and through the vents 28, thus avoiding unwanted and potentially injurious air intrusion into the human body or medical system.

In alternative embodiments that are within the scope of this invention, the shroud tabs 26 and vents 28 may be absent from the male connection means, or the standoff ribs 27 may be formed in a different shape while retaining sufficient height to provide standoff. For example, the standoff ribs 27 may take the form of pillars or posts, the distal D surfaces on which the rim of the female Luer connector would rest. In the absence of any standoff ribs 27, a vent 28 would comprise the area surrounding the nozzle base 29. Further, an embodiment that has a taper of nozzle 23 or 23*a* different from the 6% specified in the ISO 594 standard falls within the scope of this invention as would embodiments that include more than one sidecut 40 on nozzle 23*a*.

The syringe 10 can be made to have a volume of between 1 cc and 100 cc, though a volume range most commonly used for clinical applications, for example inflating balloons on trachea tubes or inflatable compression devices, would be 5 cc to 50 cc, more particularly in the 10 cc to 30 cc range. Depending on the volume, the syringe 10 may have a maximum outside diameter of between 0.5 inches and 1.5 inches, more particularly between 0.75 inches and 1.25 inches, and a length of between 2.0 inches and 5.0 inches, more particularly in the range of 2.5 to 3.5 inches measured from the distal end 30 to the proximal P side of the barrel flanges 22. For the intended use of inflating and deflating a compression device a shorter length provides the benefit of a shorter stroke length, thereby making operation easier.

The male connection means of the present invention is shown to be non-locking, in particular it has no mechanism by which the nozzle 23 or 23*a* is retained in the female connector other than by friction of the outside surfaces of the nozzle 23 or 23*a* pressing against the inside surfaces of the female connector. An alternative embodiment may include a locking mechanism, in particular, by inclusion of a thread having the characteristics of a Luer Lock thread so as to lock with female Luer Lock connectors. More particularly, this may take the form of a Luer Lock thread formed into the inside surfaces of the shroud tabs 26. In the present embodiments, the nozzle 23 or 23*a* is shown to have a taper, which may be a 6% Luer taper but nothing precludes the nozzle 23 or 23*a* from having other tapers.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope of the invention. Accordingly, while the present invention has been shown and described with reference to the foregoing embodiments of the invented apparatus and method of use, it will be apparent to those skilled in the art that other changes in form and detail may be made therein without departing from the spirit and scope of the invention as defined in the claims.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

I claim:

1. A medical system inflation syringe that enables fluid communication selective interconnectability to other medical systems or devices, by means of removable attachment to a female Luer connector that complies to the ISO 594 standard, said syringe comprising at least a plunger and a barrel, a distal end of said barrel further including a barrel lumen and a nozzle, at least one shroud tab, at least one standoff rib, at least one vent, and a nozzle base, wherein:

The nozzle further includes at least an insertion outside diameter, a lumen, and a distal opening at the nozzle's distal-most end, the lumen of the nozzle in open communication with the barrel lumen;

The at least one shroud tab is placed circumferentially around and at a distance from the nozzle and enables a friction fit between the interior wall of the at least one shroud tab and an exterior wall of the female Luer connector;

The at least one standoff rib is placed so that it extends radially from the nozzle and nozzle base to the interior wall of the at least one shroud tab;

The at least one vent is placed at the same distance from the nozzle as the at least one shroud tab and has the same height from the distal end of the barrel as said shroud tab;

The at least one vent enables a backflow of air that escapes from the connected female Luer connector that is not a swabable valve, when air is injected from the syringe into said connected female Luer connector against a resistance on the interior side of said female Luer connector;

The insertion outside diameter is located on the nozzle where the distal-most portion of the standoff rib connects to the nozzle and is less than the minimum inside diameter of any female Luer connector compliant to ISO 594 standard;

The at least one standoff rib has a height, measured from the distal end of the barrel so that when said standoff rib: i) comes into contact with the rim of the female Luer connector that is not part of a swabable valve, and the nozzle is inserted into said female Luer connector, an airtight connection between said connector and the distal opening of the nozzle is precluded, and, ii) comes into contact with the rim of the female Luer connector that is part of a swabable valve, and the nozzle is inserted into said female Luer connector, an airtight connection between said connector and the distal opening of the nozzle is established.

2. The medical system inflation syringe of claim 1 wherein the standoff rib has a height, measured from the distal end of the barrel, that is less than the heights, from the distal end of the barrel, of the at least one shroud tab and the distal-most end of the nozzle.

3. The medical system inflation syringe of claim 1 wherein the distal-most end of the nozzle further includes a lumen sidecut, at least one sidecut surround, and at least one sidecut face, wherein:

The lumen sidecut generally bisects the lumen of the nozzle along its longitudinal axis and extends proximally along the nozzle to the top-most portion of the sidecut face;

The at least one sidecut surround is located on at least a side of the lumen sidecut, thus providing air flow to and from the lumen of the barrel, in addition to only the distal opening of the nozzle, so that when the nozzle is inserted into said female Luer connector that is not a swabable valve, an airtight connection between said connector and the distal opening of the nozzle is further precluded.

4. The medical system inflation syringe of claim 1, wherein a thread, generally including at least some of the characteristics of a Luer Lock thread, is included on an inside surface of the distal-most ends of the at least one shroud tab to engage with a corresponding thread on an exterior surface of a female Luer Lock connector for further securement.

5. A male connection means for a medical system inflation syringe that enables fluid communication selective interconnectability to other medical systems or devices, by means of removable attachment to a female Luer connector, wherein said connection means includes a nozzle, at least one shroud tab, at least one standoff rib, at least one vent, and a nozzle base located on a distal end of a barrel of said inflation syringe, wherein:

The nozzle further includes at least an insertion outside diameter, a lumen, and a distal opening at the nozzle's distal-most end, the lumen of the nozzle in open communication with a barrel lumen of the barrel;

The at least one shroud tab is placed circumferentially around and at a distance from the nozzle and enable a friction fit between the interior wall of the at least one shroud tab and an exterior wall of the female Luer connector;

The at least one standoff rib is placed so that it extends radially from the nozzle and nozzle base to the interior wall of the at least one shroud tab;

The at least one vent is placed at the same distance from the nozzle as the at least one shroud tab and has the same height from the distal end of the barrel as said shroud tab;

The at least one vent enables a backflow of air that escapes from the connected female Luer connector that is not a swabable valve, when air is injected from the syringe into said connected female Luer connector against a resistance on the interior side of said female Luer connector; and, The insertion outside diameter is located on the nozzle where the distal-most portion of the standoff rib connects to the nozzle and is less than the minimum inside diameter of any female Luer connector compliant to ISO 594 standard;

The at least one standoff rib has a height, measured from the distal end of the barrel so that when said standoff rib: i) comes into contact with the rim of the female Luer connector that is not part of a swabable valve, and the nozzle is inserted into said female Luer connector, an airtight connection between said connector and the distal opening of the nozzle is precluded, and, ii) comes into contact with the rim of the female Luer connector that is part of a swabable valve, and the nozzle is inserted into said female Luer connector, an airtight connection between said connector and the distal opening of the nozzle is established.

6. The male connection means of claim 5 wherein the standoff rib has a height, measured from the distal end of the barrel, that is less than the heights, from the distal end of the barrel, of the at least one shroud tab and the distal-most end of the nozzle.

7. The male connection means of claim 5 wherein the distal-most end of the nozzle further includes a lumen sidecut, at least one sidecut surround, and at least one sidecut face, wherein:

The lumen sidecut generally bisects the lumen of the nozzle along its longitudinal axis and extends proximally along the nozzle to the top-most portion of the sidecut face;

The at least one sidecut surround is located on at least a side of the lumen sidecut, thus providing air flow to and from the lumen of the barrel, in addition to only the distal opening of the nozzle, so that when the nozzle is inserted into said female Luer connector that is not a swabable valve, an airtight connection between said connector and the distal opening of the nozzle is further precluded.

8. The male connection means of claim 5, wherein a thread, generally including at least some of the characteristics of a Luer Lock thread, is included on an inside surface of the distal-most ends of the at least one shroud tab to engage with a corresponding thread on an exterior surface of a female Luer Lock connector for further securement.

* * * * *